(12) United States Patent
Figuly et al.

(10) Patent No.: US 8,241,609 B2
(45) Date of Patent: Aug. 14, 2012

(54) METHOD FOR EMBOLIZATION USING LIQUID EMBOLIC MATERIALS

(75) Inventors: Garret D. Figuly, Wilmington, DE (US); Llewellyn Bentley Richardson, III, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 585 days.

(21) Appl. No.: 12/194,639

(22) Filed: Aug. 20, 2008

(65) Prior Publication Data

US 2009/0054535 A1  Feb. 26, 2009

Related U.S. Application Data

(60) Provisional application No. 60/966,060, filed on Aug. 24, 2007.

(51) Int. Cl.
*A61K 47/30* (2006.01)
*A61K 9/14* (2006.01)
*A61K 51/00* (2006.01)

(52) U.S. Cl. ............... 424/9.322; 424/489; 424/499; 514/772.7

(58) Field of Classification Search .............. 424/400
See application file for complete search history.

(56) References Cited

U.S. PATENT DOCUMENTS

| | | | |
|---|---|---|---|
| 4,446,261 A | 5/1984 | Yamasaki et al. | |
| 5,514,379 A * | 5/1996 | Weissleder et al. | 424/426 |
| 5,752,974 A | 5/1998 | Rhee et al. | |
| 6,218,440 B1 | 4/2001 | Kitagawa | |
| 6,379,373 B1 | 4/2002 | Sawheny et al. | |
| 6,436,424 B1 | 8/2002 | Vogel et al. | |
| 6,713,646 B2 | 3/2004 | Zhang et al. | |
| 6,884,905 B2 | 4/2005 | Zhang et al. | |
| 7,135,593 B2 | 11/2006 | Zhang et al. | |
| 7,201,918 B2 | 4/2007 | Cruise | |
| 7,834,065 B2 * | 11/2010 | Nakajima et al. | 523/111 |
| 2004/0009205 A1 | 1/2004 | Sawhney | |
| 2005/0288684 A1 * | 12/2005 | Aronson et al. | 606/108 |
| 2006/0078536 A1 * | 4/2006 | Kodokian et al. | 424/78.27 |
| 2006/0222596 A1 * | 10/2006 | Askari et al. | 424/9.41 |
| 2007/0031467 A1 * | 2/2007 | Abrahams et al. | 424/423 |
| 2007/0237742 A1 | 10/2007 | Figuly et al. | |
| 2007/0237956 A1 | 10/2007 | Figuly et al. | |
| 2007/0288052 A1 | 12/2007 | Sawhney et al. | |
| 2008/0132936 A1 | 6/2008 | Sawhney et al. | |
| 2008/0319101 A1 | 12/2008 | Nakajima et al. | |

FOREIGN PATENT DOCUMENTS

| | | |
|---|---|---|
| EP | 1849486 A1 | 10/2007 |
| JP | 60-56676 | 3/1994 |
| WO | WO0172280 A2 | 10/2001 |
| WO | WO 03/094930 A1 | 11/2003 |
| WO | WO2006080523 A1 | 8/2006 |
| WO | WO 2006086510 A2 * | 8/2006 |

OTHER PUBLICATIONS

International Search Report Dated Jan. 25, 2010, International Application No. PCT/US2008/073631.

* cited by examiner

*Primary Examiner* — Frederick Krass
*Assistant Examiner* — Dennis J Parad

(57) ABSTRACT

A method for embolization using liquid embolic materials is described. The method comprises the use of two liquid components. The first liquid component is an aqueous solution or dispersion comprising at least one oxidized polysaccharide. The second liquid component is either an aqueous solution or dispersion comprising at least one water-dispersible, multi-arm amine, or a water-dispersible multi-arm amine in the form of a neat liquid. The two components crosslink in situ to form a hydrogel that should act as an effective embolic agent.

26 Claims, No Drawings

METHOD FOR EMBOLIZATION USING LIQUID EMBOLIC MATERIALS

CROSS-REFERENCE TO RELATED APPLICATION

This application claims priority under 35 U.S.C. §119 from U.S. Provisional Application Ser. No. 60/966,060, filed Aug. 24, 2007.

FIELD OF THE INVENTION

The present invention relates to embolization. Specifically, a method is provided for embolization using two liquid components that react in situ to form a hydrogel, which should act as an effective embolic agent.

BACKGROUND OF THE INVENTION

There is a need for a degradable material for use in embolization treatment. Embolization involves the introduction of a material into the vasculature in order to block the blood flow in a particular region. This procedure may be used to treat non-cancerous tumors, such as uterine fibroids, and cancerous tumors. Vascular occlusion in the case of tumors may be used to suppress pain, limit blood loss during surgery, or to cause tumor necrosis. In addition, embolization treatment may be used to control bleeding caused by conditions such as stomach ulcers, aneurysms, and injury.

One type of embolic material is preformed hydrogel microspheres; both nondegradable and degradable hydrogel microspheres have been described.

Non-degradable hydrogel microspheres have been produced and used in tissue augmentation and embolization treatments (see for example, U.S. Pat. No. 6,218,440, U.S. Pat. No. 4,446,261, U.S. Pat. No. 6,436,424, JP1994056676A, and copending and commonly owned and commonly owned U.S. Patent Application Publication Nos. 2007/0237956 and 2007/0237742). However, a degradable embolic material could enable the administration of a number of different therapies (e.g., drug delivery and surgery) to a site without permanently occluding the site from blood flow. This could lead to more effective therapies and better patient response to treatments.

Degradable hydrogel microspheres are also known in the art. One type of degradable microsphere incorporates degradable crosslinks. As the crosslinks degrade, the microsphere breaks down into soluble polymer chains (see for example U.S. Pat. No. 6,713,646, U.S. Pat. No. 6,884,905, and WO 2003/094930). Another type of degradable microsphere is prepared from degradable polymers such as poly(lactide-co-glycolide) copolymers. One limitation of using preformed microspheres for embolization is that they cannot be delivered to small vessels.

Rhee et al. (U.S. Pat. No. 5,752,974) describe an injectable or implantable biomaterial for filling or blocking lumens or voids of the body. The injectable or implantable biomaterial is formed by reacting a polymer with a hydrophilic crosslinking agent.

Tissues adhesives formed by reacting an oxidized polysaccharide with a water-dispersible, multi-arm polyether amine have been reported (Kodokian et al., copending and commonly owned U.S. Patent Application Publication No. 2006/0078536); however, the use of the materials for embolization treatment is not described.

Therefore, the problem to be solved is to provide a degradable embolic material that can be delivered to small vessels.

The stated problem is addressed herein by the discovery that a hydrogel formed by the in situ reaction of an oxidized polysaccharide with a water dispersible, multi-arm amine may act as an effective degradable embolic material.

SUMMARY OF THE INVENTION

In various embodiments, the invention provides methods for embolization using two liquid components that react in situ to form a hydrogel, which should act as an effective embolic agent.

Accordingly, in one embodiment the invention provides a method for embolization comprising the steps of:

a) premixing
  (i) a first aqueous solution or dispersion comprising at least one oxidized polysaccharide containing aldehyde groups, having a weight-average molecular weight of about 1,000 to about 1,000,000 Daltons, said at least one oxidized polysaccharide having an equivalent weight per aldehyde group of about 90 to about 1500 Daltons, said solution or dispersion containing about 5% to about 40% by weight of said at least one oxidized polysaccharide; and
  ii) a second aqueous solution or dispersion comprising at least one water-dispersible, multi-arm amine wherein at least three of the arms are terminated by a primary amine group, wherein said at least one multi-arm amine has a number-average molecular weight of about 450 to about 200,000 Daltons, said solution or dispersion containing about 5% to about 70% by weight of said at least one multi-arm amine; or
  (iii) a water-dispersible, multi-arm amine in the form of a neat liquid wherein at least three of the arms are terminated by a primary amine group, wherein said at least one multi-arm amine has a number-average molecular weight of about 450 to about 200,000 Daltons; to form a mixture; and b) introducing said mixture into the vasculature of the mammal before said mixture completely cures.

In another embodiment, the invention provides a method for embolization comprising the step of:

introducing into the vasculature of said mammal:

i) a first aqueous solution or dispersion comprising at least one oxidized polysaccharide containing aldehyde groups, having a weight-average molecular weight of about 1,000 to about 1,000,000 Daltons, said at least one oxidized polysaccharide having an equivalent weight per aldehyde group of about 90 to about 1500 Daltons, said solution or dispersion containing about 5% to about 40% by weight of said at least one oxidized polysaccharide; and (ii) a second aqueous solution or dispersion comprising at least one water-dispersible, multi-arm amine wherein at least three of the arms are terminated by a primary amine group, wherein said at least one multi-arm amine has a number-average molecular weight of about 450 to about 200,000 Daltons, said solution or dispersion containing about 5% to about 70% by weight of said at least one multi-arm amine; or (iii) a water-dispersible, multi-arm amine in the form of a neat liquid wherein at least three of the arms are terminated by a primary amine group, wherein said at least one multi-arm amine has a number-average molecular weight of about 450 to about 200,000 Daltons;

wherein (i) and (ii) or (iii) react to form a hydrogel.

DETAILED DESCRIPTION

Disclosed herein is a method for embolization using liquid embolic materials. The method comprises the use of two liquid components. The first liquid component is an aqueous solution or dispersion comprising at least one oxidized polysaccharide. The second liquid component is either an aqueous solution or dispersion comprising at least one water-dispersible, multi-arm amine, or a water-dispersible multi-arm amine in the form of a neat liquid. The two components crosslink in situ to form a hydrogel that should act as an effective embolic agent.

The method disclosed herein has several potential advantages for use in embolization treatment. The two components that react to form the hydrogel are in liquid form and, therefore, may be delivered via very small catheters to areas where particle embolics may not be deliverable. The hydrogels are tissue adhesive and should provide good strength as an occlusion. Moreover, the two components that react to form the hydrogel and the resulting hydrogel are already known to be biocompatible (Kodokian et al. SUPRA). Additionally, the hydrogels can be configured to provide desired degradation and provide an embolic agent that is not permanent.

The following definitions are used herein and should be referred to for interpretation of the claims and the specification.

The term "embolization" refers to a medical treatment to partially or totally occlude blood vessels.

The term "oxidized polysaccharide" refers to a polysaccharide that has been reacted with an oxidizing agent to introduce aldehyde groups into the molecule.

The term "equivalent weight per aldehyde group" refers to the weight-average molecular weight of an oxidized polysaccharide divided by the number of aldehyde groups introduced in the molecule.

The term "water-dispersible, multi-arm amine" refers to a polymer having three or more polymer chains ("arms"), which may be linear or branched, emanating from a central structure, which may be a single atom, a core molecule, or a polymer backbone, wherein at least three of the branches ("arms") are terminated by a primary amine group. The water-dispersible, multi-arm amine is water soluble or is able to be dispersed in water to form a colloidal suspension capable of reacting with a second reactant in aqueous solution or dispersion.

The term "water-dispersible, multi-arm polyether amine" refers to a branched polyether, wherein at least three of the branches ("arms") are terminated by a primary amine group, which is water soluble or able to be dispersed in water to form a colloidal suspension capable of reacting with a second reactant in aqueous solution or dispersion.

The term "polyether" refers to a polymer having the repeat unit [—O—R]—, wherein R is a hydrocarbylene group having 2 to 5 carbon atoms.

The term "branched polyether" refers to a polyether having one or more branch points ("arms"), including star, dendritic, comb, highly branched, and hyperbranched polyethers.

The term "dendritic polyether" refers to a highly branched polyether having a branching structure that repeats regularly with each successive generation of monomer, radiating from a core molecule.

The term "comb polyether" refers to a multi-arm polyether in which linear side chains emanate from trifunctional branch points on a linear polymer backbone.

The term "star polyether" refers to a multi-arm polyether in which linear side chains emanate from a single atom or a core molecule having a point of symmetry.

The term "highly branched polyether" refers to a multi-arm polyether having many branch points, such that the distance between branch points is small relative to the total length of the arms.

The term "hyperbranched polyether" refers to a multi-arm polyether that is more branched than highly branched with order approaching that of an imperfect dendritic polyether.

The term "multi-arm branched end amine" refers to a water dispersible, multi-arm amine wherein at least three of the polymer chains ("arms") have two or three branched ends, each of which is terminated by a primary amine group.

The term "multi-functional amine" refers to a chemical compound comprising at least two functional groups, at least one of which is a primary amine group.

The term "% by weight", also referred to herein as "wt %", refers to the weight percent relative to the total weight of the solution or dispersion, unless otherwise specified.

The term "hydrogel" refers to a water-swellable polymeric matrix, consisting of a three-dimensional network of macromolecules held together by covalent or non-covalent crosslinks, that can absorb a substantial amount of water to form an elastic gel.

Oxidized Polysaccharides

Polysaccharides useful in the invention include, but are not limited to, dextran, starch, agar, cellulose, and hyaluronic acid. These polysaccharides are available commercially from sources such as Sigma Chemical Co. (St Louis, Mo.) and Pharmacosmos A/S (Holbaek, Denmark). In one embodiment, the polysaccharide is dextran. Typically, commercial preparations of polysaccharides are a heterogeneous mixture having a distribution of different molecular weights, and are characterized by various molecular weight averages, for example, the weight-average molecular weight ($M_w$), or the number-average molecular weight ($M_n$), as is known in the art. Suitable polysaccharides have a weight-average molecular weight of about 1,000 to about 1,000,000 Daltons, and in addition about 3,000 to about 250,000 Daltons.

The polysaccharide is oxidized to introduce aldehyde groups using any suitable oxidizing agent, including but not limited to, periodates, hypochlorites, ozone, peroxides, hydroperoxides, persulfates, and percarbonates. For example, the polysaccharide may be oxidized by reaction with sodium periodate as described by Mo et al. (*J. Biomater. Sci. Polymer Edn.* 11:341-351, 2000). The polysaccharide may be reacted with different amounts of periodate to give polysaccharides with different degrees of oxidation and therefore, different amounts of aldehyde groups, as described in detail in the General Methods Section of the Examples herein. The oxidation does not alter the average molecular weight of the polysaccharide significantly. Therefore, the weight-average molecular weight of the oxidized polysaccharides useful in the invention is about 1,000 to about 1,000,000 Daltons, and in addition about 3,000 to about 250,000 Daltons. Suitable oxidized polysaccharides include, but are not limited to, oxidized dextran, oxidized starch, oxidized agar, oxidized cellulose, and oxidized hyaluronic acid. In one embodiment, the oxidized polysaccharide is oxidized dextran.

The aldehyde content of the oxidized polysaccharide may be determined using methods known in the art. For example, the dialdehyde content of the oxidized polysaccharide may be determined using the method described by Hofreiter et al. (*Anal Chem.* 27:1930-1931, 1955), as described in detail in the General Methods Section of the Examples herein. In that method, the amount of alkali consumed per mole of dialdehyde in the oxidized polysaccharide, under specific reaction conditions, is determined by a pH titration. Additionally, the dialdehyde content of the oxidized polysaccharide may be determined using nuclear magnetic resonance spectroscopy (NMR).

In one embodiment, the equivalent weight per aldehyde group of the oxidized polysaccharide is about 90 to about 1500 Daltons.

In one embodiment, the oxidized polysaccharide is oxidized dextran having a weight-average molecular weight of 8,500 to 11,500 Daltons and an equivalent weight per aldehyde group of about 146 Daltons. In another embodiment, the oxidized polysaccharide is oxidized dextran having a weight-average molecular weight of 60,000 to 90,000 Daltons and an equivalent weight per aldehyde group of about 322 Daltons.

In the method disclosed herein, the oxidized polysaccharide is used in the form of an aqueous solution or dispersion, referred to herein as "the first aqueous solution or dispersion". Dispersion, as used herein, refers to a colloidal suspension capable of reacting with a second reactant in an aqueous medium. To prepare the first aqueous solution or dispersion, at least one oxidized polysaccharide is added to water to give a concentration of about 5% to about 40% by weight, in addition about 15% to about 30% by weight relative to the total weight of the solution or dispersion. Mixtures of different oxidized polysaccharides containing aldehyde groups, having different average molecular weights and/or different equivalent weights per aldehyde group, may also be used. If a mixture of different oxidized polysaccharides is used, the total concentration of the oxidized polysaccharides is about 5% to about 40% by weight, in addition about 15% to about 30% by weight, relative to the total weight of the solution or dispersion. The optimal concentration to be used depends on the intended application and on the concentration of the water dispersible, multi-arm amine used, as described below, and can be readily determined by one skilled in the art using routine experimentation.

For use in embolization, it is preferred that the first aqueous solution or dispersion be sterilized to prevent infection. Any suitable sterilization method known in the art that does not degrade the polysaccharide may be used, including, but not limited to, electron beam irradiation, gamma irradiation, ethylene oxide sterilization, or ultra-filtration through a 0.2 μm pore membrane.

The first aqueous solution or dispersion may further comprise various additives. For example, the first aqueous solution or dispersion may comprise at least one additive selected from pH modifiers, viscosity modifiers, antimicrobials, colorants, surfactants, pharmaceutical drugs, therapeutic agents, and radio-opaque compounds. The amount of the additive used depends on the particular application and may be readily determined by one skilled in the art using routine experimentation.

For example, the first aqueous solution or dispersion may optionally include at least one pH modifier to adjust the pH of the solution or dispersion. Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, nitrogen-containing compounds other than primary and secondary amines, and basic carbonates and phosphates.

The first aqueous solution or dispersion may optionally include at least one thickener. The thickener may be selected from among known viscosity modifiers, including, but not limited to, polysaccharides and derivatives thereof, such as starch or hydroxyethyl cellulose.

The first aqueous solution or dispersion may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The first aqueous solution or dispersion may also optionally include at least one colorant to enhance the visibility of the solution or dispersion. Suitable colorants include dyes, pigments, and natural coloring agents. Examples of suitable colorants include, but are not limited to, FD&C and D&C colorants, such as FD&C Violet No. 2, D&C Green No. 6, D&C Green No. 5, D&C Violet No. 2; and natural colorants such as beetroot red, canthaxanthin, chlorophyll, eosin, saffron, and carmine.

The first aqueous solution or dispersion may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the first aqueous solution or dispersion may optionally include pharmaceutical drugs or therapeutic agents, such as anti-angiogenic factors, anti-inflammatory drugs, analgesics, anti-coagulation agents, coagulation agents, clotting agents, local anesthetics, and the like. Suitable pharmaceutical drugs and therapeutic agents that may be incorporated into the first aqueous solution or dispersion are known in the art, for example, see Vogel et al., U.S. Patent Application Publication No. 2003/0211165, in particular paragraphs 0132 through 0161 which are incorporated herein by reference.

Additionally, the first aqueous solution or dispersion may optionally include radio-opaque compounds, such as barium sulfate and gold particles.

Water-Dispersible, Multi-Arm Amines:

Suitable water dispersible, multi-arm amines include, but are not limited to, water dispersible multi-arm polyether amines, amino-terminated dendritic polyamidoamines, and multi-arm branched end amines. Typically, the water dispersible, multi-arm amines have a number-average molecular weight of about 450 to about 200,000 Daltons, in addition from about 2,000 to about 40,000 Daltons.

In one embodiment, the water dispersible, multi-arm amine is a multi-arm polyether amine, which is a water-dispersible polyether having the repeat unit [—O—R]—, wherein R is a hydrocarbylene group having 2 to 5 carbon atoms. The term "hydrocarbylene group" refers to a divalent group formed by removing two hydrogen atoms, one from each of two different carbon atoms, from a hydrocarbon. Suitable water dispersible, multi-arm polyether amines include, but are not limited to, dendritic, comb, star, highly branched, and hyperbranched polyethers wherein at least three of the arms are terminated by a primary amine group. Examples of water-dispersible, multi-arm polyether amines include, but are not limited to, amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, polyoxyalkylene triamines (sold under the trade name Jeffamine® triamines, by Huntsman LLC., Houston, Tex.), and multi-arm branched end polyether amines. Examples of star polyethylene oxide amines, include, but are not limited to, various multi-arm polyethylene glycol amines, available from Nektar Transforming Therapeutics (Huntsville, Ala.), and star polyethylene glycols having 3, 4, 6, or 8 arms terminated with primary amines (referred to herein as 3, 4, 6 or 8-arm star PEG amines, respectively). Examples of suitable Jeffamine® triamines include, but are not limited to, Jeffamine® T-403 (CAS No. 39423-51-3), Jeffamine® T-3000 (CAS No. 64852-22-8), and Jeffamine® T-5000 (CAS No. 64852-22-8).

In one embodiment, the water-dispersible multi-arm polyether amine is an eight-arm polyethylene glycol having eight arms, each arm being terminated by a primary amine group, and having a number-average molecular weight of about 10,000 Daltons.

In another embodiment, the water-dispersible multi-arm polyether amine is a four-arm polyethylene glycol having four arms, each arm being terminated by a primary amine group, and having a number-average molecular weight of about 2,000 Daltons.

The water dispersible, multi-arm polyether amines are either available commercially, as noted above, or may be prepared using methods known in the art. For example, multi-arm polyethylene glycols, wherein at least three of the arms are terminated by a primary amine group, may be prepared by putting amine ends on multi-arm polyethylene glycols (e.g., 3, 4, 6 and 8-arm star polyethylene glycols, available from companies such as Nektar Transforming Therapeutics; SunBio, Inc., Anyang City, South Korea; NOF Corp., Tokyo, Japan; or JenKem Technology USA, Allen, Tex.) using the method described by Buckmann et al. (*Makromol. Chem.* 182:1379-1384, 1981). In that method, the multi-arm polyethylene glycol is reacted with thionyl bromide to convert the hydroxyl groups to bromines, which are then converted to amines by reaction with ammonia at 100° C. The method is broadly applicable to the preparation of other water dispersible, multi-arm polyether amines. Additionally, water dispersible, multi-arm polyether amines may be prepared from multi-arm polyethers using the method described by Chenault (copending and commonly owned U.S. Patent Application Publication No. 2007/0249870). In that method, the multi-arm polyether is reacted with thionyl chloride to convert the hydroxyl groups to chlorine groups, which are then converted to amines by reaction with aqueous or anhydrous ammonia. Other methods that may used for preparing water dispersible, multi-arm polyether amines are described by Merrill et al. in U.S. Pat. No. 5,830,986, and by Chang et al. in WO 97/30103.

The water dispersible, multi-arm amine may also be an amino-terminated dendritic polyamidoamine, sold under the trade name Starburst® Dendrimers (available from SigmaAldrich, St Louis, Mo.).

The water dispersible, multi-arm amine may also be a multi-arm branched end amine, as described by Arthur (copending and commonly owned Patent Application No. PCT/U.S.07/24393, WO 2008/066787). The multi-arm branched end amines are water dispersible, multi-arm amines wherein at least three of the arms have two or three branched ends, each of which is terminated by a primary amine group. The multiplicity of functional groups increases the statistical probability of reaction at a given chain end and allows more efficient incorporation of the molecules into a polymer network. The starting materials used to prepare the multi-arm branched end amines may be branched polymers such as multi-arm polyether polyols including, but not limited to, comb and star polyether polyols. The multi-arm branched end amines can be prepared by attaching multiple amine groups to the ends of the polymer by reaction with the hydroxyl groups using methods well known in the art. For example, a multi-arm branched end amine having two amine functional groups at the end of the polymer arms can prepared by reacting the starting material, as listed above, with thionyl chloride in a suitable solvent such as toluene to give the chloride derivative, which is subsequently reacted with tris(2-aminoethyl) amine to give the multi-arm branched end amine. In one embodiment, the multi-arm branched end amine is a multi-arm branched end polyether amine.

It should be recognized that the water dispersible, multi-arm amines are generally a somewhat heterogeneous mixture having a distribution of arm lengths and in some cases, a distribution of species with different numbers of arms. When a water dispersible, multi-arm amine has a distribution of species having different numbers of arms, it can be referred to based on the average number of arms in the distribution. For example, in one embodiment the water dispersible, multi-arm amine is an 8-arm star PEG amine, which comprises a mixture of multi-arm star PEG amines, some having less than and some having more than 8 arms; however, the multi-arm star PEG amines in the mixture have an average of 8 arms. Therefore, the terms "8-arm", "6-arm", "4-arm" and "3-arm" as used herein to refer to water dispersible, multi-arm amines, should be construed as referring to a heterogeneous mixture having a distribution of arm lengths and in some cases, a distribution of species with different numbers of arms, in which case the number of arms recited refers to the average number of arms in the mixture.

For use in embolization, the water dispersible, multi-arm amine may be used in the form of an aqueous solution or dispersion, or as a neat liquid (i.e., 100% by weight) in the case of a water dispersible, multi-arm amine that exists as a liquid.

In one embodiment, the water dispersible, multi-arm amine is used in the form of an aqueous solution or dispersion, referred to herein as "the second aqueous solution or dispersion". To prepare the second aqueous solution or dispersion, at least one water dispersible, multi-arm amine is added to water to give a concentration of about 5% to about 70% by weight, in addition from about 20% to about 50% by weight relative to the total weight of the solution or dispersion. Mixtures of different water dispersible, multi-arm amines having different number-average molecular weights, different numbers of arms, or different number-average molecular weights and different numbers of arms may be used. If a mixture of different water dispersible, multi-arm amines is used, the total concentration of the water dispersible, multi-arm amines is about 5% to about 70% by weight, in addition from about 20% to about 50% by weight relative to the total weight of the solution or dispersion. The optimal concentration to be used depends on the intended application and on the concentration of the oxidized polysaccharide used and can be readily determined by one skilled in the art using routine experimentation.

For use in embolization, it is preferred that the second aqueous solution or dispersion be sterilized to prevent infection. Any of the methods described above for sterilizing the first aqueous solution or dispersion may be used.

The second aqueous solution or dispersion may further comprise various additives. Any of the additives described above for the first aqueous solution or dispersion may be used.

Additionally, the second aqueous solution or dispersion may comprise at least one multi-functional amine having one or more primary amine groups to provide other beneficial properties, such as hydrophobicity or modified crosslink density. Suitable multi-functional amines are described by Kodokian et al. in copending and commonly owned U.S. Patent Application Publication No. 2006/0078536, specifically paragraph 0047 which is incorporated herein by reference.

In another embodiment, the water dispersible, multi-arm amine is used in the form of a neat liquid, referred to herein as "the neat liquid". Examples of suitable water dispersible, multi-arm amines that may be used as a neat liquid include the four-arm polyethylene glycol having four arms, each arm being terminated by a primary amine group, having a number-average molecular weight of about 2,000 Daltons; and the Jeffamine® triamines, as described above. For use in embolization, it is preferred that the neat liquid be sterilized to prevent infection. Any of the methods described above for sterilizing the first aqueous solution or dispersion may be used.

Method of Embolization

In the method for embolization disclosed herein, the first aqueous solution or dispersion comprising at least one oxidized polysaccharide and the second aqueous solution or dispersion comprising at least one water dispersible, multi-arm amine, or a water dispersible, multi-arm amine in the form of a neat liquid, are introduced into the vasculature of a mammal where they crosslink in situ to form a hydrogel. Once formed, the hydrogel should effectively block the blood flow distal to the occlusion site. The occlusion site may be any target site where, for medical treatment, it is desired to block the flow of blood. For example, the occlusion site may be in a blood vessel that feeds a tumor such as a uterine fibroid or a cancerous tumor, in an arteriovenous malformation, or in a blood vessel where the blood is not contained, such as in the case of a stomach ulcer or injury. Preoperative embolization may also be performed to stop blood flow to a region targeted for surgery.

The first aqueous solution or dispersion and the second aqueous solution or dispersion, or the neat liquid may be introduced into the vasculature of a mammal in a variety of ways. The amount of the material introduced depends on a number of variables, such as the size of the blood vessel to be occluded, and may be determined by one skilled in the art using routine experimentation. Because the components are both liquids, they can be delivered readily to small blood vessels; however, large blood vessels may be effectively occluded as well.

In one embodiment, the first aqueous solution or dispersion and the second aqueous solution or dispersion, or the neat liquid are premixed and the resulting mixture is introduced into the vasculature using methods known in the art. For example, the two liquids may be premixed using a double barrel syringe equipped with a mixing tip, such as that available form ConProtec, Inc. (Salem, N.H.) or Mixpac Systems AG (Rotkreuz, Switzerland), and introduced into the vasculature using a catheter or endoscope. Additionally, devices for mixing a two liquid component tissue adhesive and delivering the resulting mixture endoscopically are known in the art and may be adapted for the mixing and delivery of the two liquid components disclosed herein (see for example, Nielson, U.S. Pat. No. 6,723,067; and Redl et al., U.S. Pat. No. 4,631,055). In this embodiment, the gelation time of the mixture of the components is adjusted so that the hydrogel does not form in the delivery device. The gelation time may be controlled in various ways, for example, by varying the concentration of the oxidized polysaccharide and the water dispersible, multi-arm amine used, by varying the relative levels of functional groups present on these respective reactants, and by adding a chemical additive that comprises at least one reactive group capable of reacting with an amine or an aldehyde group, as described by Figuly et al. in copending and commonly owned U.S. patent application Ser. No. 12/145,737. Suitable chemical additives include, but are not limited to, primary amines, such as glucosamine and 2-aminoethanol; secondary amines, such as diisopropylamine; aldose sugars, such as D-glucose and D-mannose; ketose sugars, such as D-ribulose, D-fructose, D-glyceraldehyde, and dihydroxyacetone; Brønsted acids, such as hydrochloric acid, acetic acid, and carboxylic acids; acid salts, such as glucosamine hydrochloride and 2-aminoethanol hydrochloride; Brønsted bases such as sodium hydroxide and potassium hydroxide; amino acids, such as lysine, cysteine, arginine, and serine; short peptides having 2 to about 15 amino acids; activated esters, such as N-hydroxysuccinimidyl ester, sulfo-succinimidyl acetate, and methyl acetimidate hydrochloride; and activated halides, such as allyl chloride, benzyl bromide, butyryl chloride, and 2,4-dinitrofluorobenzene.

In another embodiment, the first aqueous solution or dispersion and the second aqueous solution or dispersion, or the neat liquid are introduced into the vasculature simultaneously where they mix to form a hydrogel which should occlude the blood vessel. The two liquids may be introduced into the vasculature in various ways, for example, using a dual-lumen catheter, such as those available from Bistech, Inc. (Woburn, Mass.). Additionally, injection devices for introducing two liquid components endoscopically into the body simultaneously are known in the art and may be adapted for the delivery of the two liquid components disclosed herein (see for example, Linder et al., U.S. Pat. No. 5,322,510).

One of the advantages of the hydrogel disclosed herein as an embolic material is that it is degradable, and therefore should not occlude the blood vessel permanently. This would enable the administration of a number of different therapies (e.g., drug and surgery) to a site without permanently occluding the site, which could lead to more effective therapies and better patient response to treatments. The degradation rate of the hydrogel may be controlled in various ways, for example, by varying the concentration of the oxidized polysaccharide and the water dispersible, multi-arm amine used, by varying the relative levels of functional groups present on these respective reactants, and by adding a chemical additive that comprises at least one reactive group capable of reacting with an amine or an aldehyde group, as described by Figuly et al., SUPRA. The conditions required to obtain the optimum degradation rate for any particular application may be determined by one skilled in the art using routine experimentation.

The embolic material disclosed herein may also be used to deliver a drug or therapeutic agent to the embolization site by adding the desired agent to at least one of the two aqueous solutions or dispersions, as described above.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "mL" means milliliter(s), "L" means liter(s), "μL" means microliter(s), "cm" means centimeter(s), "mm" means millimeter(s), "μm" means micrometer(s), "mol" means mole(s), "mmol" means millimole(s), "g" means gram(s), "mg" means milligram(s), "wt %" means percent by weight, "mol %" means mole percent, "Vol" means volume, "v/v" means volume per volume, "Da" means Daltons, "kDa" means kilo-Daltons, "MWCO" means molecular weight cut-off, "kPa" means kilopascals, "ID" means internal diameter, the designation "10K" means that a polymer molecule possesses an average molecular weight of about 10 kiloDaltons, a designation of "60K" indicates an average molecular weight of about 60 kiloDaltons, etc., "NMR" means nuclear magnetic resonance spectroscopy, "$M_n$" means number-average molecular weight, "mw" means molecular weight, "M" means molar concentration, "PEG" means polyethylene glycol.

A reference to "Aldrich" or a reference to "Sigma" means the said chemical or ingredient was obtained from Sigma-Aldrich, St. Louis, Mo.

General Methods:

Reagents:

The 8-arm PEG ($M_n$=10,000, referred to herein as "8-arm PEG 10K"), having eight arms, each terminated by a hydroxyl group, and the 4-arm PEG ($M_n$=2,000, referred to herein as "4-arm PEG 2K"), having four arms, each terminated by a hydroxyl group were purchased from NOF America Corp. (White Plains, N.Y.).

Dextran having a weight-average molecular weight of 8,500-11,500 Da and dextran having a weight-average molecular weight of 60,000-90,000 Da were purchased from Sigma.

Preparation of Oxidized Dextran:

The following procedure was used to prepare an oxidized dextran, also referred to herein as dextran aldehyde, with about 50% aldehyde content conversion from dextran having a weight-average molecular weight of 8,500-11,500 Da. This dextran aldehyde is referred to herein as D10-50. Other aldehyde conversions were obtained by varying the concentration of the periodate solution used. Likewise dextrans of other molecular weights were oxidized to provide the corresponding oxidized dextran. Specifically, the following dextran aldehydes were prepared: weight-average molecular weight of 8,500-11,500 Da with an oxidation conversion of 50%, equivalent weight per aldehyde group of about 146 Daltons (D10-50), and weight-average molecular weight of 60,000-90,000 Da with an oxidation conversion of 24%, equivalent weight per aldehyde group of about 322 Daltons (D60-24).

Dextran (19.0 g; 0.12 mol saccharide rings; average molecular weight of 8,500-11,500 Da; Sigma, product number D9260) was added to 170 g of distilled water in a 500 mL round bottom flask. The mixture was stirred for 15 to 30 min to produce a solution; then a solution of 17.7 g (0.083 mol; mw=213.9) sodium periodate in 160 g of distilled water was added to the dextran solution all at once. The mixture was stirred at room temperature for 5 h. After this time, the solution was removed from the round bottom flask, divided into four equal volumes and dispensed into 4 dialysis membrane tubes (MWCO=3500 Da). The tubes were dialyzed in deionized water for 4 days, during which time the water was changed twice daily. The aqueous solutions were removed from the dialysis tubes, placed in wide-mouth polyethylene containers and frozen using liquid nitrogen, and lyophilized to afford white, fluffy oxidized dextran.

The dialdehyde content in the resulting oxidized dextran was determined using the following procedure. The oxidized dextran (0.1250 g) was added to 10 mL of 0.25 M NaOH in a 250 mL Erlenmeyer flask. The mixture was gently swirled and then placed in a temperature-controlled sonicator bath at 40° C. for 5 min until all the material dissolved, giving a dark yellow solution. The sample was removed from the bath and the flask was cooled under cold tap water for 5 min. Then 15.00 mL of 0.25 M HCl was added to the solution, followed by the addition of 50 mL of distilled water and 1 mL of 0.2% phenolphthalein solution. This solution was titrated with 0.25 M NaOH to an endpoint determined by a color change from yellow to purple/violet. The same titration was carried out on a sample of the starting dextran to afford a background aldehyde content. The dialdehyde content, also referred to herein as the oxidation conversion or the degree of oxidation, in the oxidized dextran sample was calculated using the following formula:

$$\text{Dialdehyde Content} = \frac{(Vb - Va)_s}{W_s/M} - \frac{(Vb - Va)_p}{W_p/M} \times 100\%$$

Vb=total meq of base

Va=total meq of acid

W=dry sample weight (mg)

M=weight-average molecular weight of polysaccharide repeat unit (=162 for dextran)

s=oxidized sample p=original sample

Preparation of Peg Amines:

Preparation of 8-Arm Polyethylene Glycol 10K Octaamine (P8-10-1):

An 8-arm PEG 10K octaamine, referred to herein as "P8-10-1," was synthesized using the two-step procedure described by Chenault in co-pending and commonly owned U.S. Patent Application Publication No. 2007/0249870. A typical synthesis is described here. In the first step, the 8-arm PEG 10K was converted to an 8-Arm PEG 10K chloride by reaction with thionyl chloride, i.e.,

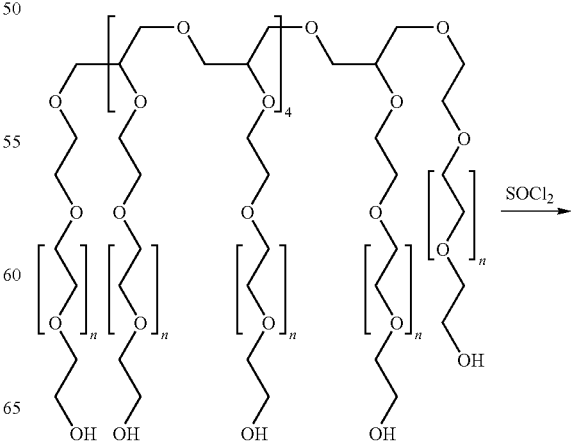

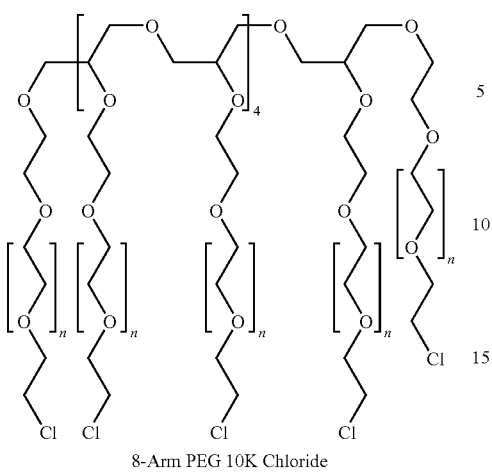

8-Arm PEG 10K Chloride n = 25

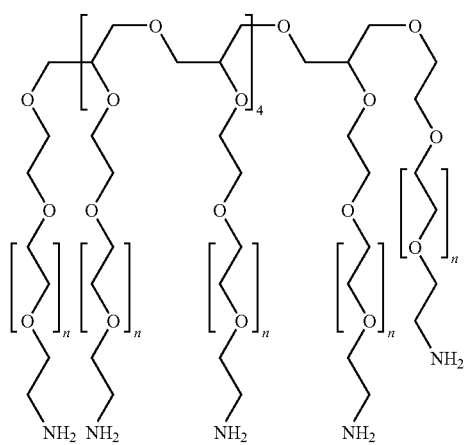

8-Arm PEG 10K Amine n = 25

The 8-arm PEG 10K (NOF Sunbright HGEO-10000; 1000 g in a 3-L round-bottom flask) was dried by dissolving it in 1.5 L of toluene and distilling 500 mL of toluene-water azeotrope plus toluene under reduced pressure (2 kPa) with a pot temperature of 60° C., adding another 500 mL of toluene to the pot, and distilling 500 mL of toluene-water azeotrope plus toluene under reduced pressure (2 kPa) with a pot temperature of 60° C.

The solution of 8-arm PEG was allowed to cool to room temperature. Then, thionyl chloride (233 mL, 3.19 mol) was added to the flask, which was equipped with a reflux condenser, and the mixture was heated at 85° C. with stirring under a blanket of nitrogen for 4 h. Excess thionyl chloride and most of the toluene were removed by vacuum distillation at 2 kPa (bath temperature 40-60° C.). Two successive 500-mL portions of toluene were added and evaporated under reduced pressure (2 kPa, bath temperature 80-85° C.) to complete the removal of thionyl chloride. The final crude product was dissolved in 1000 g of de-ionized water.

In the second step, the 8-Arm PEG 10K chloride was converted to the 8-Arm PEG 10K amine by reaction with aqueous ammonia, i.e.,

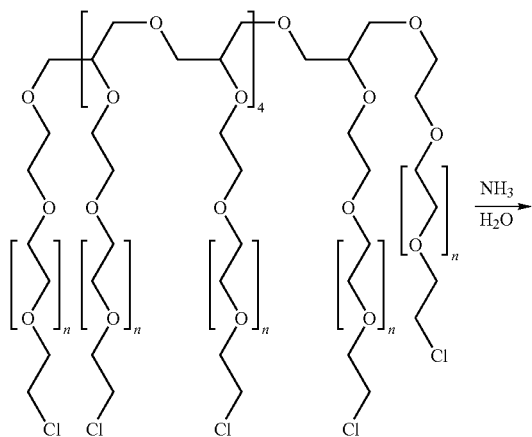

The aqueous solution of 8-arm PEG-Cl prepared above, was dissolved in 16 L of concentrated aqueous ammonia (28 wt %) and heated in a sealed stainless steel pressure vessel at 60° C. for 48 h. The solution was sparged for 24 h with dry nitrogen and then placed under reduced pressure for 3 h to drive off ammonia. The solution was then passed through a column of strongly basic anion exchange resin (5 kg; Purolite® A-860, The Purolite Co., Bala-Cynwyd, Pa.) in the hydroxide form. The eluant was collected, and two 7-L portions of de-ionized water were passed through the column and collected. The aqueous fractions were combined, concentrated under reduced pressure (2 to 0.3 kPa, bath temperature 60° C.) to give the 8-Arm PEG 10K octaamine. The final product was characterized by proton NMR and size exclusion chromatography (SEC), as described by Chenault, SUPRA.

Preparation of 4-Arm Polyethylene Glycol 2K Tetraamine (P4-2-1):

A 4-arm PEG 2K tetraamine, referred to herein as "P4-2-1," was prepared using a similar procedure as described above for the 8-arm PEG 10K octaamine. A typical synthesis is described here. In the first step, the 4-arm PEG 2K was converted to a 4-arm PEG 2K chloride by reaction with thionyl chloride, i.e.,

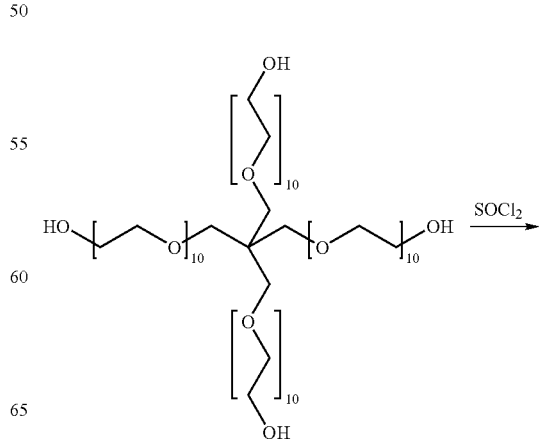

-continued

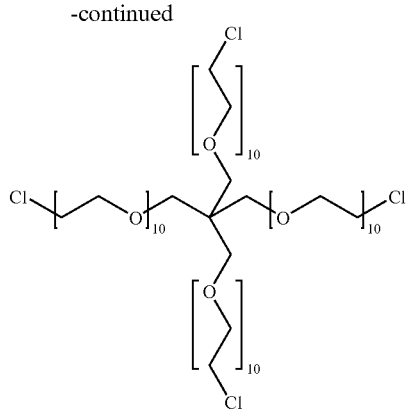

The 4-arm PEG 2K (NOF Sunbright PTE-2000; 1000 g in a 3-L round-bottom flask) was dried by dissolving it in 600 mL of toluene and distilling off the toluene-water azeotrope plus toluene under reduced pressure (2 kPa) with a pot temperature of 42° C., adding another 600 mL of toluene to the pot, and repeating the azeotropic distillation. The dried 4-arm PEG was dissolved in 1000 mL of toluene and 1.50 g (20 mmol) of N,N-dimethylformamide, and the solution was warmed to 60-65° C. Then, thionyl chloride (584 mL, 8.00 mol) was added to the flask, which was equipped with a reflux condenser, and the mixture was heated at 85° C. with stirring under a blanket of nitrogen for 2 h. Excess thionyl chloride and most of the toluene were removed by vacuum distillation at 2 kPa (bath temperature 40° C.). Two successive 600-mL portions of toluene were added and evaporated under reduced pressure (2 to 0.3 kPa, bath temperature 40-85° C.) to complete the removal of thionyl chloride.

In the second step, the 4-arm PEG 2K chloride was converted to the 4-arm PEG 2K amine by reaction with aqueous ammonia, i.e.,

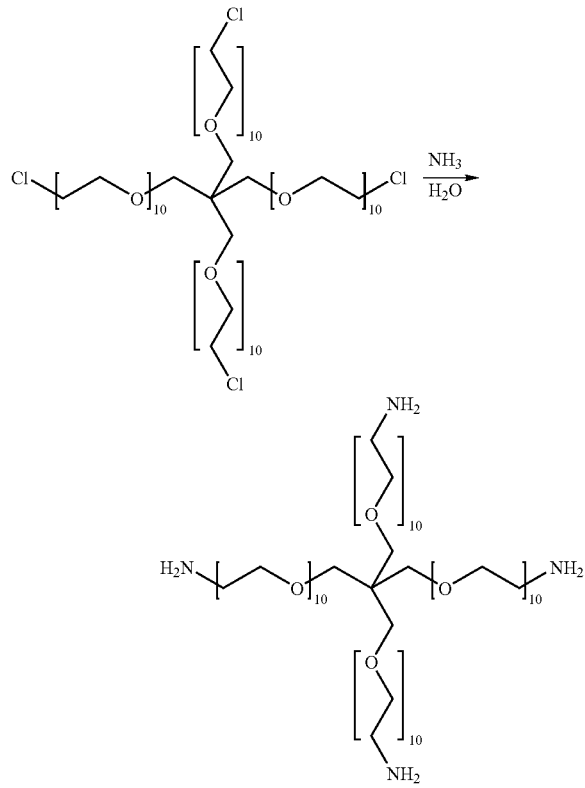

The 4-arm PEG-Cl (1000 g) was dissolved in 16 L of concentrated aqueous ammonia (28 wt %) and heated in a sealed stainless steel pressure vessel at 60° C. for 48 h. The solution was sparged for 24 h with dry nitrogen and then placed under reduced pressure for 2 h to drive off ammonia. The solution was then passed through a column of strongly basic anion exchange resin (5 kg, Purolite® A-860) in the hydroxide form. The eluant was collected, and two 7-L portions of de-ionized water were passed through the column and collected. The aqueous fractions were combined, concentrated under reduced pressure (2 to 0.3 kPa, bath temperature 60° C.) to give the 4-arm PEG 2K tetraamine. The final product was characterized by proton NMR and size exclusion chromatography (SEC), as described by Chenault, SUPRA.

Examples 1-5

Dextran Aldehyde/Multi-Arm PEG-Amine Hydrogels as Embolic Agents

The purpose of these Examples was to demonstrate the use of dextran aldehyde/multi-arm PEG amine hydrogels as embolization agents.

A bench-top pressure testing system, as described below, was used to test the effectiveness of the hydrogels as embolic agents. The system was equipped with silicone tubing to mimic flexible blood vessels. A syringe was connected to apply pressure to silicone tubing of various sizes (see Table 1), obtained from MSC Industrial Supply Co., Melville, N.Y. A pressure transducer with readout in the line was used to measure pressure in mm of mercury (Hg). The system was filled with 0.9% NaCl to mimic the ionic strength of physiological media (e.g., blood). A dual barrel syringe filled with an aqueous dextran aldehyde solution and an aqueous multi-arm PEG amine solution was used with an 8-step mixer to mix the two solutions and permit sufficient gel time to deliver the material into the saline-filled tubing. The two aqueous solutions were prepared by adding the dextran aldehyde and the water dispersible, multi-arm PEG amine to deionized water to give the desired concentration (see Table 1). After injection into the silicone tubing, the hydrogel was allowed to cure for a given time, after which the dual barrel syringe was removed. A syringe containing saline solution at the other end of the tubing was used to apply pressure gradually until a leak developed through the hydrogel plug. The maximum pressure maintained was recorded.

TABLE 1

Experimental Conditions for Embolic Testing

| Example | Dextran Aldehyde Solution | Multi-Arm PEG Amine Solution | Silicone Tubing ID (mm) | Plug Size Delivered (cm) | Cure Time (min) |
| --- | --- | --- | --- | --- | --- |
| 1 | D10-50 10 wt % | P8-10-1/P4-2-1 (9:1 ratio) 30 wt % | 1.6 | 8.9 | 2.5 |
| 2 | D10-50 10 wt % | P8-10-1/P4-2-1 (9:1 ratio) 30 wt % | 1.6 | 2.5 | 2.5 |
| 3 | D10-50 10 wt % | P8-10-1/P4-2-1 (9:1 ratio) 30 wt % | 1.6 | 7.5 | 2.5 |
| 4 | D10-50 10 wt % | P8-10-1/P4-2-1 (9:1 ratio) 30 wt % | 3.2 | 10 | 3 |
| 5 | D60-24 17 wt % | P8-10-1 30 wt % | 3.2 | 7.5 | 3 |

The results are given in Table 2. In all of the Examples, the hydrogels successfully occluded the silicone tubing. Pressures greater than 200 mm Hg (26.7 kPa) were considered successful because this pressure exceeds physiological pressures in the vasculature. The results demonstrate that the dextran aldehyde/multi-arm PEG amine hydrogels should be usable as embolic agents to occlude small or large vessels.

TABLE 2

Results of Embolic Testing

| Example | Maximum Pressure mm Hg | Observations |
|---|---|---|
| 1 | >1000 (>133 kPa) | no leaks or breakthroughs |
| 2 | >1000 (>133 kPa) | no leaks or breakthroughs |
| 3 | 675 (90.0 kPa) | small leak observed, pressure continued to rise after leak detected up to >800 mm Hg (107 kPa) |
| 4 | 450 (60.0 kPa) | small leak observed, pressure continued to rise after leak detected up to 523 mm Hg (69.7 kPa) |
| 5 | 250 (33.3 kPa) | small leak observed, pressure continued to rise after leak detected up to 570 mm Hg (76.0 kPa) |

What is claimed is:

1. A method for embolization of vasculature in a mammal comprising the steps of:
  a) providing (i) a first aqueous solution or dispersion comprising at least one oxidized polysaccharide containing aldehyde groups, having a weight-average molecular weight of about 3,000 to about 250,000 Daltons, said at least one oxidized polysaccharide having an equivalent weight per aldehyde group of about 90 to about 1500 Daltons, said solution or dispersion containing about 5% to about 40% by weight of said at least one oxidized polysaccharide;
  b) providing (ii) a second aqueous solution or dispersion comprising at least one water-dispersible, multi-arm amine selected from the group consisting of a water dispersible multi-arm polyether amine, an amino-terminated dendritic polyamidoamine, and a multi-arm branched end amine, wherein at least three of the arms are terminated by a primary amine group, wherein said at least one multi-arm amine has a number-average molecular weight of about 450 to about 200,000 Daltons, said solution or dispersion containing about 5% to about 70% by weight of said at least one multi-arm amine; or
    (iii) a water-dispersible, multi-arm amine selected from the group consisting of a water dispersible multi-arm polyether amine, an amino-terminated dendritic polyamidoamine, and a multi-arm branched end amine, in the form of a neat liquid wherein at least three of the arms are terminated by a primary amine group, wherein said at least one multi-arm amine has a number-average molecular weight of about 450 to about 200,000 Daltons;
  c) mixing (i) and (ii) or (i) and (iii) to form a mixture; and
  d) introducing said mixture into the vasculature of the mammal before said mixture completely cures;
    wherein said mixture forms a degradable hydrogel in said vasculature, and wherein (i) and (ii) or (i) and (iii) are combined in a relative proportion to achieve a desired degradation rate of the degradable hydrogel.

2. The method according to claim 1 wherein the water dispersible, multi-arm amine has a number-average molecular weight from about 2,000 to about 40,000 Daltons.

3. The method according to claim 1 wherein the at least one oxidized polysaccharide is selected from the group consisting of oxidized dextran, oxidized starch, oxidized agar, oxidized cellulose, and oxidized hyaluronic acid.

4. The method according to claim 3 wherein the at least one oxidized polysaccharide is oxidized dextran.

5. The method according to claim 4 wherein the oxidized dextran has a weight-average molecular weight of 8,500 to 11,500 Daltons and an equivalent weight per aldehyde group of about 146 Daltons.

6. The method according to claim 4 wherein the oxidized dextran has a weight-average molecular weight of 60,000 to 90,000 Daltons and an equivalent weight per aldehyde group of about 322 Daltons.

7. The method according to claim 1 wherein at least one of the first aqueous solution or dispersion or the second aqueous solution or dispersion further comprises an additive selected from the group consisting of pH modifiers, viscosity modifiers, antimicrobials, colorants, surfactants, pharmaceutical drugs, therapeutic agents, and radio-opaque compounds.

8. The method according to claim 7 wherein at least one of the first aqueous solution or dispersion or the second aqueous solution or dispersion further comprises a pharmaceutical drug or therapeutic agent.

9. The method according to claim 1 wherein the first aqueous solution or dispersion contains about 15% to about 30% by weight of the at least one oxidized polysaccharide.

10. The method according to claim 1 wherein the water-dispersible multi-arm polyether amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, polyoxyalkylene triamines, and multi-arm branched end polyether amines.

11. The method according to claim 10 wherein the water-dispersible multi-arm polyether amine is a polyethylene glycol comprising eight arms, each arm being terminated by a primary amine group, and having a number-average molecular weight of about 10,000 Daltons.

12. The method according to claim 10 wherein the water-dispersible multi-arm polyether amine is a polyethylene glycol comprising four arms, each arm being terminated by a primary amine group, and having a number-average molecular weight of about 2,000 Daltons.

13. The method according to claim 1 wherein the second aqueous solution or dispersion contains about 20% to about 50% by weight of the water dispersible, multi-arm amine.

14. A method for embolization of vasculature in a mammal comprising the steps of:
  a) providing (i) a first aqueous solution or dispersion comprising at least one oxidized polysaccharide containing aldehyde groups, having a weight-average molecular weight of about 3,000 to about 250,000 Daltons, said at least one oxidized polysaccharide having an equivalent weight per aldehyde group of about 90 to about 1500

Daltons, said solution or dispersion containing about 5% to about 40% by weight of said at least one oxidized polysaccharide;
b) providing (ii) a second aqueous solution or dispersion comprising at least one water-dispersible, multi-arm amine selected from the group consisting of a water dispersible multi-arm polyether amine, an amino-terminated dendritic polyamidoamine, and a multi-arm branched end amine, wherein at least three of the arms are terminated by a primary amine group, wherein said at least one multi-arm amine has a number-average molecular weight of about 450 to about 200,000 Daltons, said solution or dispersion containing about 5% to about 70% by weight of said at least one multi-arm amine; or
(iii) a water-dispersible, multi-arm amine selected from the group consisting of a water dispersible multi-arm polyether amine, an amino-terminated dendritic polyamidoamine, and a multi-arm branched end amine, in the form of a neat liquid wherein at least three of the arms are terminated by a primary amine group, wherein said at least one multi-arm amine has a number-average molecular weight of about 450 to about 200,000 Daltons; and
c) introducing (i) and (ii) or (i) and (iii) into the vasculature of said mammal where (i) and (ii) or (i) and (iii) react in said vasculature to form a degradable hydrogel;
wherein (i) and (ii) or (i) and (iii) are combined in a relative proportion to achieve a desired degradation rate of the hydrogel.

15. The method according to claim 14 wherein the water dispersible, multi-arm amine has a number-average molecular weight from about 2,000 to about 40,000 Daltons.

16. The method according to claim 14 wherein the at least one oxidized polysaccharide is selected from the group consisting of oxidized dextran, oxidized starch, oxidized agar, oxidized cellulose, and oxidized hyaluronic acid.

17. The method according to claim 16 wherein the at least one oxidized polysaccharide is oxidized dextran.

18. The method according to claim 17 wherein the oxidized dextran has a weight-average molecular weight of 8,500 to 11,500 Daltons and an equivalent weight per aldehyde group of about 146 Daltons.

19. The method according to claim 17 wherein the oxidized dextran has a weight-average molecular weight of 60,000 to 90,000 Daltons and an equivalent weight per aldehyde group of about 322 Daltons.

20. The method according to claim 14 wherein at least one of the first aqueous solution or dispersion or the second aqueous solution or dispersion further comprises an additive selected from the group consisting of pH modifiers, viscosity modifiers, antimicrobials, colorants, surfactants, pharmaceutical drugs, therapeutic agents, and radio-opaque compounds.

21. The method according to claim 20 wherein at least one of the first aqueous solution or dispersion or the second aqueous solution or dispersion further comprises a pharmaceutical drug or therapeutic agent.

22. The method according to claim 14 wherein the first aqueous solution or dispersion contains about 15% to about 30% by weight of the at least one oxidized polysaccharide.

23. The method according to claim 14 wherein the water-dispersible multi-arm polyether amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, polyoxyalkylene triamines, and multi-arm branched end polyether amines.

24. The method according to claim 23 wherein the water-dispersible multi-arm polyether amine is a polyethylene glycol comprising eight arms, each of said arms being terminated by a primary amine group, and having a number-average molecular weight of about 10,000 Daltons.

25. The method according to claim 23 wherein the water-dispersible multi-arm polyether amine is a polyethylene glycol comprising four arms, each of said arms being terminated by a primary amine group, and having a number-average molecular weight of about 2,000 Daltons.

26. The method according to claim 14 wherein the second aqueous solution or dispersion contains about 20% to about 50% by weight of the water dispersible, multi-arm amine.

* * * * *